United States Patent [19]

Pawliszyn

[11] Patent Number: 5,759,370
[45] Date of Patent: Jun. 2, 1998

[54] METHOD AND DEVICE FOR ISOELECTRIC FOCUSING WITHOUT CARRIER AMPHOLYTES

[76] Inventor: Janusz B. Pawliszyn, 383 Dunvegan Drive, Waterloo, Ontario, Canada, N2K 1W7

[21] Appl. No.: 309,595

[22] Filed: Mar. 24, 1995

Related U.S. Application Data

[63] Continuation-in-part of Ser. No. 26,635, Mar. 5, 1993, abandoned.

[51] Int. Cl.[6] ........................................................ C25B 9/00
[52] U.S. Cl. .......................... 204/459; 204/451; 204/601; 204/610
[58] Field of Search .......................... 204/459, 610, 204/601, 451

[56] References Cited

U.S. PATENT DOCUMENTS

| | | | |
|---|---|---|---|
| 3,664,939 | 5/1972 | Luner et al. | 204/183.2 |
| 4,725,343 | 2/1988 | Hjerten et al. | 204/183.2 |
| 5,110,434 | 5/1992 | Zhu et al. | 204/183.2 |
| 5,324,413 | 6/1994 | Gordon | 204/299 R |

*Primary Examiner*—Cecilia J. Tsang
*Assistant Examiner*—C. Delacroix-Muirheid
*Attorney, Agent, or Firm*—Daryl W. Schnurr

[57] ABSTRACT

A device and method for isoelectric focusing of ampholytes in a buffer uses a cone-shaped capillary with a positive electrode connected at a narrow end and a negative electrode connected at the wide end of the capillary. The electrical potential across the buffer creates a temperature gradient which, in turn, creates a pH gradient. The electric current also creates an electric field gradient which focuses the ampholytes. Previous devices and methods use carrier ampholytes or use temperature baths to create a temperature gradient.

28 Claims, 7 Drawing Sheets

METHOD AND DEVICE FOR ISOELECTRIC FOCUSING WITHOUT CARRIER AMPHOLYTES

This is a continuation-in-part application of application Ser. No. 08/026,635 filed Mar. 5, 1993, now abandoned.

BACKGROUND OF THE INVENTION

1. Field of the Invention

This invention relates to a device and method for isoelectric focusing of ampholytes contained in a buffer. The focusing facilitates fractionation of ampholytic components.

2. Description of the Prior Art

Isoelectric focusing is an electrophoretic method that has been used previously to separate ampholyte analytes, such as proteins, based on differences in their isoelectric points. Analytes are placed in an electrostatic field produced in a medium such as agarose gel with a well-defined pH gradient. Analytes are initially protonated and deprotonated depending on the pH of the buffer in which they are located and they migrate in the electrostatic field towards their respective isoelectric points where the net charge of the analytes is zero and therefore their mobility is nil. Ampholyte analytes can be concentrated and focused in narrow zones frequently giving resolution between analyte bands better than 0.01 pH units. Isoelectric focusing using capillaries has advantages over the gel format because of superior speed and because the capillary can have an inside diameter as small as 5 μm which allows analysis of very small samples. When a capillary is used, a pH gradient is created using carrier ampholytes, which are polyaminopolycarboxylic acids. These carrier ampholytes are expensive and introduce complexity in purifying the proteins. In addition, they interfere with ultraviolet detection. It is also known to create a pH gradient, which results from a temperature gradient, by using a system of two circulating baths at different temperatures attached to each end of the separation vessel. Unfortunately, the temperatures are not stable due to Joulean heating and this procedure is very inconvenient. In all of the prior art methods that do not use carrier ampholytes, the pH gradient is created separately from an electric current that is used for the actual separation or fractionation of the ampholytes.

SUMMARY OF THE INVENTION

It is an object of the present invention to provide a device and method of isoelectric focusing and fractionation where an electric current is used to create a temperature gradient along a separation vessel and that same electric current is used to create an electric field gradient for isoelectric focusing and fractionation. It is a further object of the present invention to provide a device and method for isoelectric focusing and fractionation where a temperature gradient is created due to the physical characteristics of a separation vessel using a power source that generates a constant current.

A device used for isoelectric focusing of ampholytes contained in a buffer has an elongated separation vessel with two ends. The vessel contains the buffer and the vessel has an elongated tapered portion so that a temperature gradient can be created within contents of the vessel using a power source that generates a constant current. The power source has one terminal connected at one end of the vessel and another terminal connected at the other end of the vessel. The power source is connected to provide means with said tapered portion to create a temperature gradient longitudinally along the buffer in said vessel between said ends and to simultaneously focus said ampholytes, with a detection system to monitor progress of said focusing.

A method of isoelectric focusing of ampholytes contained in a buffer uses an elongated separation vessel with two ends. The vessel has physical characteristics such that a temperature gradient can be created longitudinally within contents of the vessel using a constant current from a power source. The power source and an imaging detection system are arranged to monitor progress of said focusing. The method comprises the steps of filling the vessel with a buffer containing ampholytes, connecting the power source to create a temperature gradient longitudinally along said buffer in said vessel and monitoring the progress of said focusing using said detection system.

A method of fractionating ampholytic components of biological material contained in a buffer uses an elongated separation vessel with two ends. The vessel has physical characteristics such that a temperature gradient can be created within contents of the vessel using a constant current generated by a power source having one terminal connected at one end of said vessel and the other terminal connected at the other end. There is a reservoir for the terminals at each end of the vessel. One of the reservoirs is a cathodic reservoir and the other reservoir is an anodic reservoir. There are several separate anodic reservoirs. The method comprises the steps of activating the current until all components of the buffer having a pI, which is low enough, pass through the vessel into a first anodic reservoir, replacing the first anodic reservoir with a second anodic reservoir and activating the system with a slightly lower current than that which was used with the first reservoir, thereby causing part of the ampholytes located by focusing at one end of the vessel and having a low enough pI to be charged negatively and to migrate into the second anodic container, replacing the second anodic container with a third anodic container and repeating the process with an even lower current to cause another part of the ampholytes located by focusing at one end of the vessel with a low enough pI to migrate into the third anodic container, continuing to repeat the process with successive anodic containers and successive reductions in current until sufficient fractions of ampholytic components are obtained.

BRIEF DESCRIPTION OF THE DRAWINGS

In the drawings:

FIG. 3b is a graph of a temperature gradient along the capillary of FIG. 3a;

DESCRIPTION OF A PREFERRED EMBODIMENT

Figure 1:
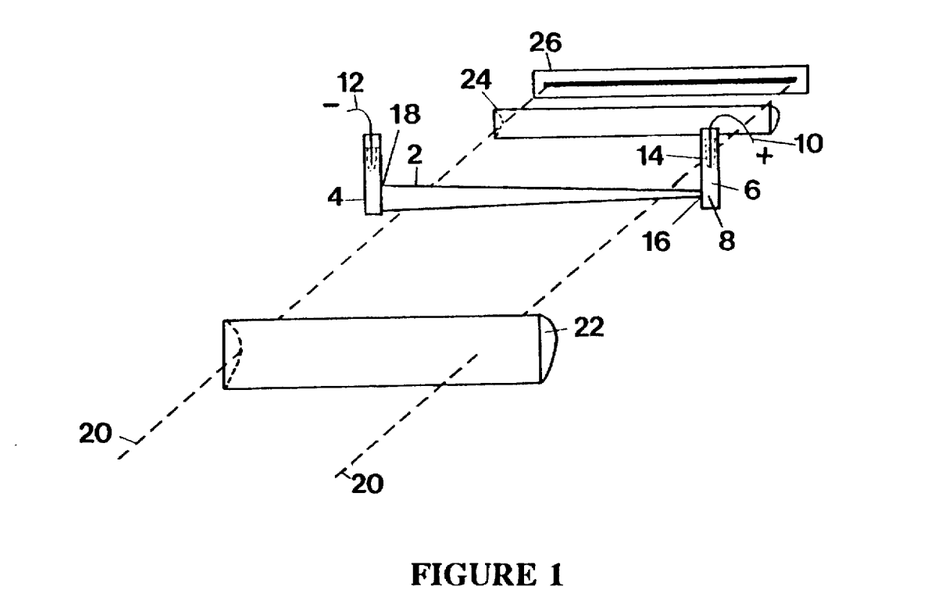
FIG. 1 is a schematic perspective view of part of an isoelectric focusing system.

In FIG. 1, an elongated separation vessel 2 has two ends with a reservoir 4, 6 at each end. The vessel and the reservoirs contain a buffer 8. The buffer is either a mixture of a weak acid and conjugated base or a weak base and conjugated acid (usually in water). A power source (not shown) that generates a constant current has one terminal 10 connected at one end of said vessel 2 and another terminal 12 connected at another end of said vessel 2. The power source is connected to create a temperature gradient along the buffer 8 in the vessel 2. Simultaneously, the electric current created by the power source will produce an electric field gradient required for isoelectric focusing on ampholytic components. A membrane 14 is an ultrafiltration membrane that surrounds the electrodes to prevent access of proteins or other substances in the buffer to the surface of the electrodes so that absorption, oxidation, reduction or degradation will not occur. The vessel 2 has physical characteristics so that a temperature gradient will be created within the buffer 8 when the power source is connected to pass a constant electric current through the vessel. The vessel 2 is a cone-shaped capillary having a narrow end 16 and a wide end 18. A positive terminal is connected into the reservoir 6 at the narrow end 16 and a negative terminal 12 is connected into the reservoir 4 at the wide end 18. The tapered shape of the capillary causes a temperature gradient to be created within the buffer from one end of the capillary to the other. The temperature gradient in turn causes a pH gradient to be created. The capillary shown in the drawings has side walls that extend between two ends that are smoothly tapered from one end to the other. The capillary has a linear taper but a capillary having a non-linear taper could be used.

When the electric current is passed through the buffer, the narrow end of the capillary gets hotter than the wide end 18, creating a temperature gradient along the buffer. The electric field gradient created by the presence of the current focuses or fractionates the ampholytes with ampholytes having the same isoelectric point moving to the same zone of the capillary. No carrier ampholytes are required to be used.

A detection system monitors progress of the focusing. The detection system consists of a light source (not shown in FIG. 1) which generates a light beam 20. The light beam 20 passes through a cylindrical lens 22 through the capillary, which is transparent, and through a lens 24 to a sensor 26. The sensor 26 determines the differences in an absorption signal of the light beam as it passes through the capillary.

Figure 2:
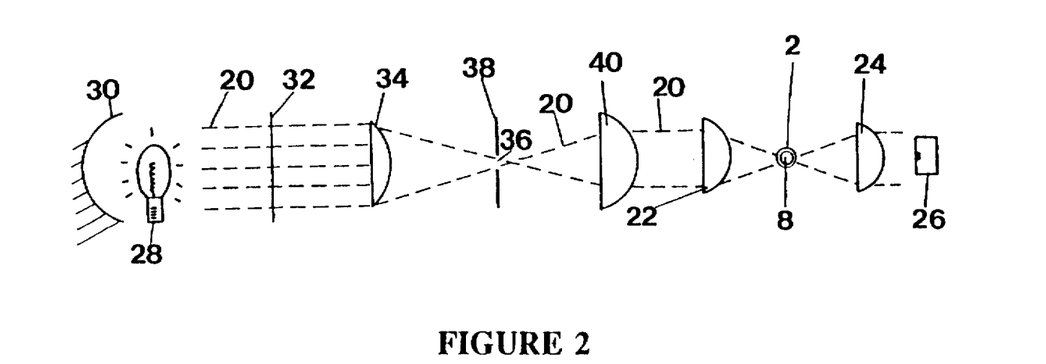
FIG. 2 is a schematic side view of an isoelectric focusing system.

In FIG. 2, a more detailed schematic drawing of the capillary or separation vessel 2 and the detection system is shown with the same components that are shown in FIG. 1 being designated by the same reference numeral. In FIG. 2, a light source 28 has a reflector 30 on one side and produces the light beam 20 which is directed through a filter 32. After the filter 32, the beam 20 passes through a focusing lens 34, which focuses the beam on a pinhole 36 in a partition 38. After passing through the pinhole, the beam 20 passes through a collecting lens 40 and then through the cylindrical lens 22 which focuses the beam on the capillary 2. After passing through the capillary 2 and the buffer 8 contained within the capillary 2, the beam passes through the lens 24 and is directed onto the sensor 26 where the magnitude of the absorption signal is measured continuously.

Preferably, the power supply is a DC power supply having a high voltage of approximately 1 kV. Preferably, the voltage ranges from 100 volts per cm of length of the separation vessel to 1 kV per cm of length of the separation vessel.

Figure 3A:
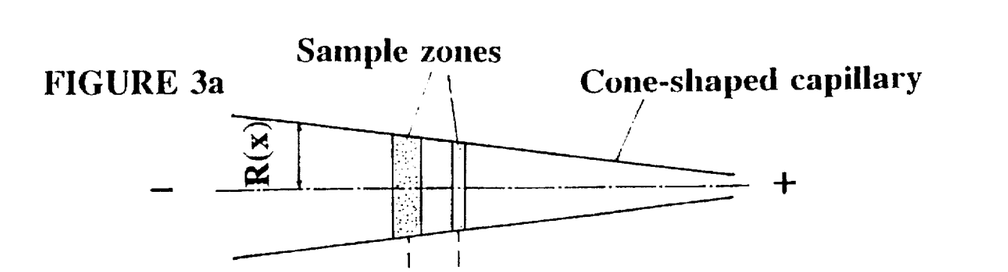
FIG. 3a is a schematic side view of a cone-shaped capillary with ampholytes separated into sample zones.
Figure 3B:
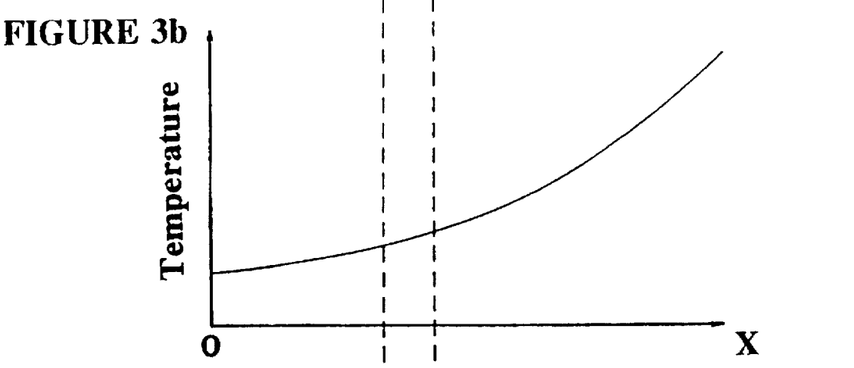
Figure 3C:
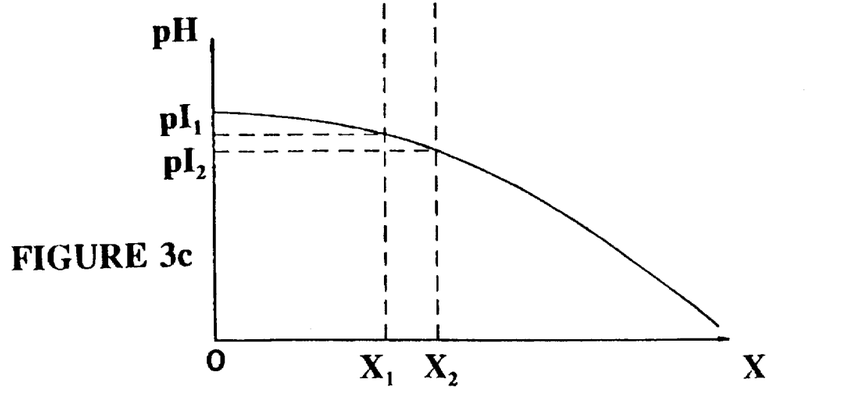
FIG. 3c is a graph of the pH gradient along a length of the capillary.

From FIGS. 3a, 3b and 3c, it can be seen that the capillary gets much hotter at the narrow end than at the wide end and that pH is much lower at the narrow end than at the wide end.

The amount of heat generated per unit length of the separation vessel filled with the electrolyte buffer at a dimension x is $dQ(x)/dx$ and is proportional to the electrophoretic current, I, and the magnitude of the electric field along the separation vessel at this dimension $\{E(x)\}$. In other words:

$$\frac{dQ}{dx}(x) = E(x)I$$

The value of the electrophoretic current I is constant along the capillary axis (see FIG. 3a) and can be calculated from:

$$I = \kappa A(x) E(x)$$

where $A(x)$ is a cross-section area of the separation channel at given dimension x and $\kappa$ is the electrolyte conductivity and therefore:

$$\frac{dQ}{dx}(x) = \frac{I^2}{\kappa A(x)}$$

For cone-shaped capillary geometry of the separation vessel the relationship is:

$$\frac{dQ}{dx}(x) = \frac{I^2}{\kappa \pi R^2(x)}$$

where $R(x)$ is the capillary radius at given dimension x.

The above equation clearly indicates that by reducing the capillary diameter along the capillary axis, the amount of heat generated in the system is increasing rapidly which results in the temperature gradient in the capillary as shown in FIG. 3b. The exact temperature profile is produced in the cone-shaped capillaries can be calculated by solving the differential equation describing heat transfer in the system and considering appropriate electrolyte flows.

Since the dissociation constant of a weak acid or base, which determines the pH of the buffer, is a thermodynamic property the thermal gradient generated inside the cone-shaped capillary produces a corresponding pH gradient as shown in FIG. 3c.

Figure 4:
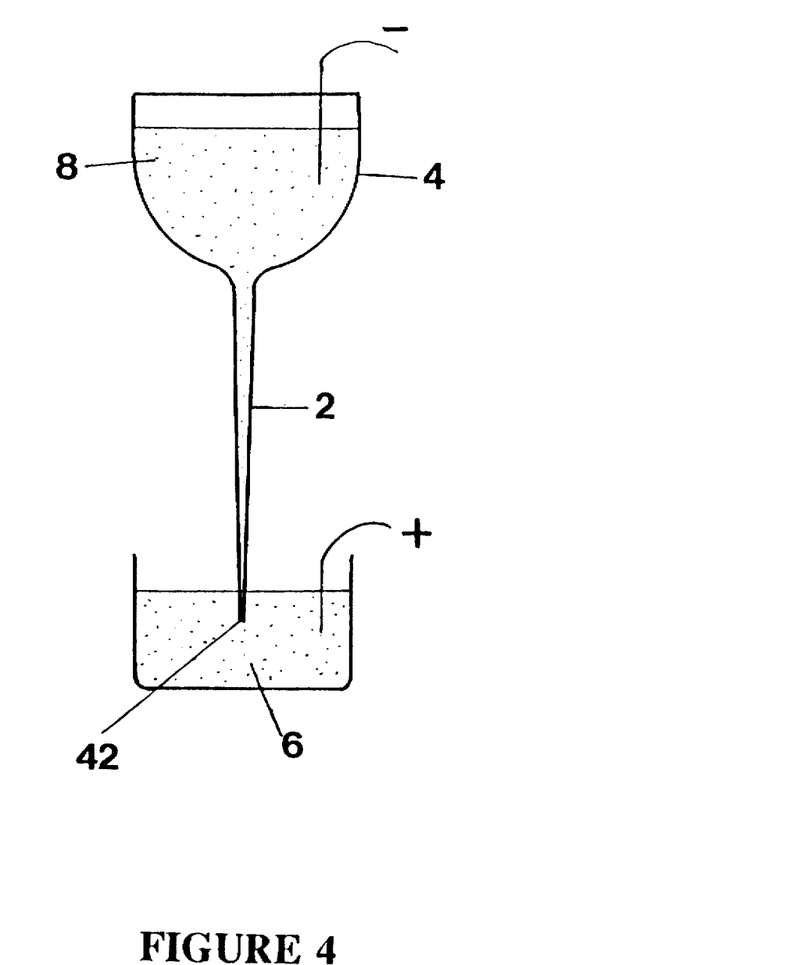
FIG. 4 is a side view of a cone-shaped capillary with a reservoir at each end.

In FIG. 4, there is shown a device which can be used to rapidly concentrate and purify small amounts of biological material prior to analysis. In a first step, an upper reservoir 4 is filled with ampholytes contained in a buffer 8. The reservoir 6 at the lower end of the vessel 2 has a positive terminal from the power source (not shown) connected therein. The reservoir 4 has a negative or ground terminal from the same power source connected therein. After application of separation voltage, target proteins within the buffer 8 are concentrated and focused inside the cone-shaped capillary 2 which is uncoated. Then, that part of the sample containing the positively charged ampholytes (the pI of which is higher than the buffer pH) and neutral species is removed from the reservoir 4. Then, the content of the capillary is emptied for collection. The electroosmotic flow, which flows from the lower to upper reservoir prevents the neutral species from entering the capillary, but it also slows down the focusing process. A positive pressure can be applied to the upper reservoir 4 or a vacuum to the lower reservoir 6 to increase hydrodynamic flow in the capillary. The device shown in FIG. 4 can also be used to fractionate ampholytic components of biological material when using several anodic containers (only one of which is shown in FIG. 4). Initially, all sample components, for which pI is low enough to allow passage through the capillary, will be collected in a first reservoir 6 and will constitute a first fraction. Then, the first anodic container 6 will be replaced with a second anodic container (not shown) and a tip 42 of the capillary 2 will be placed in the second container and the current in the system will be slightly lowered, thereby lowering the temperature in the tip 42. The current is lowered by lowering the potential. This will cause an increase in pH in the buffer in the tip. Proteins within the capillary, which have a low enough pI and are located at the very tip of the capillary, will be charged negatively and will migrate to the second anodic container. This process can be repeated several times by successively lowering the current still further to fractionate biological material focused and concentrated inside the cone-shaped capillary to create further fractions as desired. The process can be performed in a continuous and automated fashion and can be used for concentration fractionation and separation.

Figure 5:
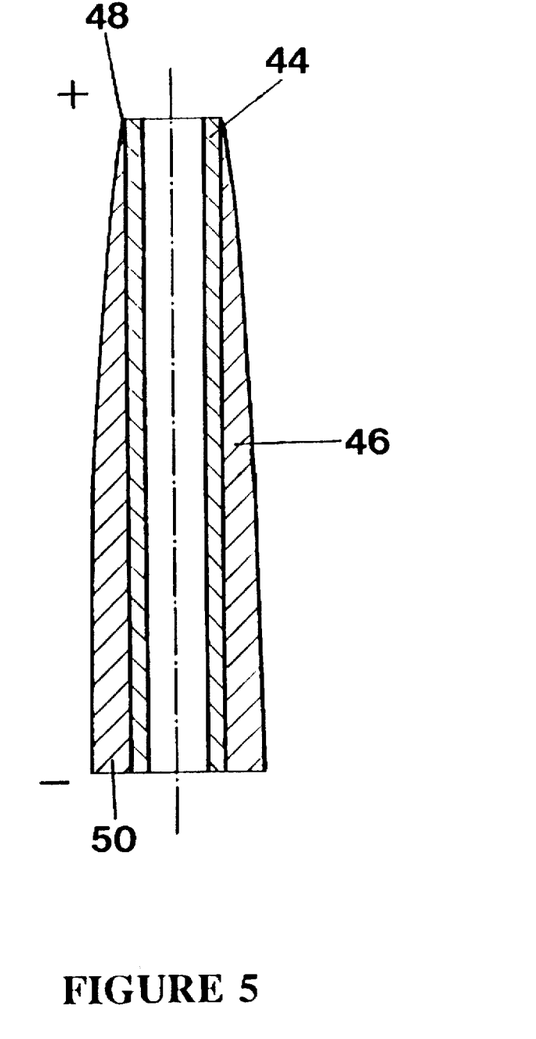
FIG. 5 is a sectional side view of a capillary having a constant inside diameter and a conductor of varying thickness.

In FIG. 5, a separation vessel 44 has a constant inside diameter but a conductive outer wall 46 of varying thickness. When electrodes are connected to the wall 46 with a positive electrode connected at a narrow end 48 and a negative or ground electrode connected at a wide end 50 and a constant current is passed through the wall 46, a temperature gradient is created in the same manner as the temperature gradient for the separation vessel 2 shown in FIG. 1 except that the electrodes are connected to the conducting wall 46 as well as being connected into the buffer within the vessel. A temperature gradient is created within the wall 46 and the heat from the wall 46 is conducted into the buffer within the vessel 44 to create a similar temperature gradient within the buffer. The positive electrode (not shown) is connected to the narrow end of the wall 46 and the negative electrode (not shown) is connected to the wide end of the wall 46. While a single power source is preferred to create said temperature gradient and to focus said ampholytes, separate power sources could be used, one for the wall 46 and one for isoelectric focusing.

Figure 6:
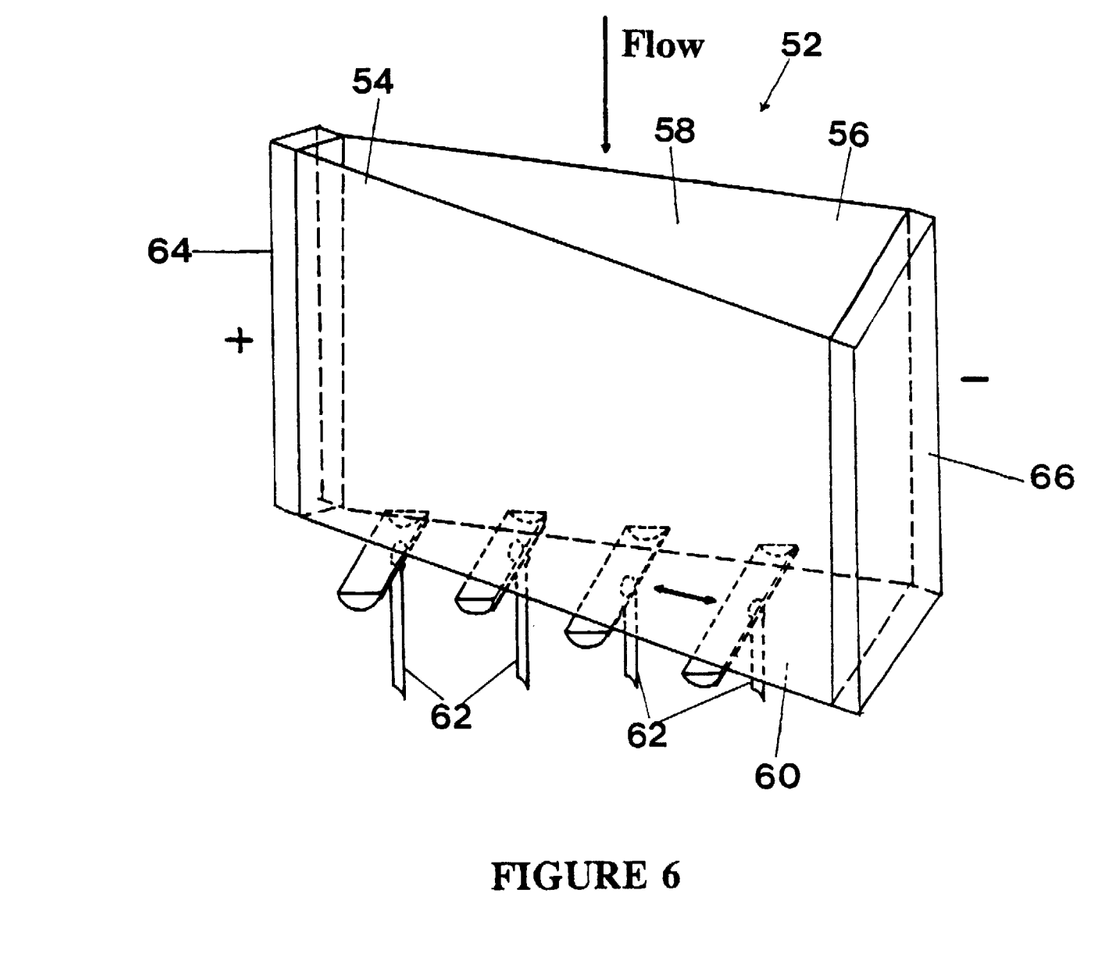
FIG. 6 is a schematic perspective view of a continuous flow separation vessel having a V-shaped cross-section.

In FIG. 6, there is shown a continuous flow separation vessel 52 having two non-parallel walls 54, 56. The walls converge with one another so that the vessel has a V-shaped cross-section with an inlet 58 and an outlet 60 so that a buffer can flow into and out of said vessel continuously in a direction normal to said cross-section. Collectors 62 at the outlet 60 collect part of the buffer that contains focused ampholytes of interest in the location along the length of the vessel where the collectors are located. While the electrodes are not shown in FIG. 6, the positive electrode would be connected into the buffer at a narrow end 64 and the negative electrode would be connected into the buffer at the wide end 66. The end walls themselves could be membrane protected electrodes.

Figure 7:
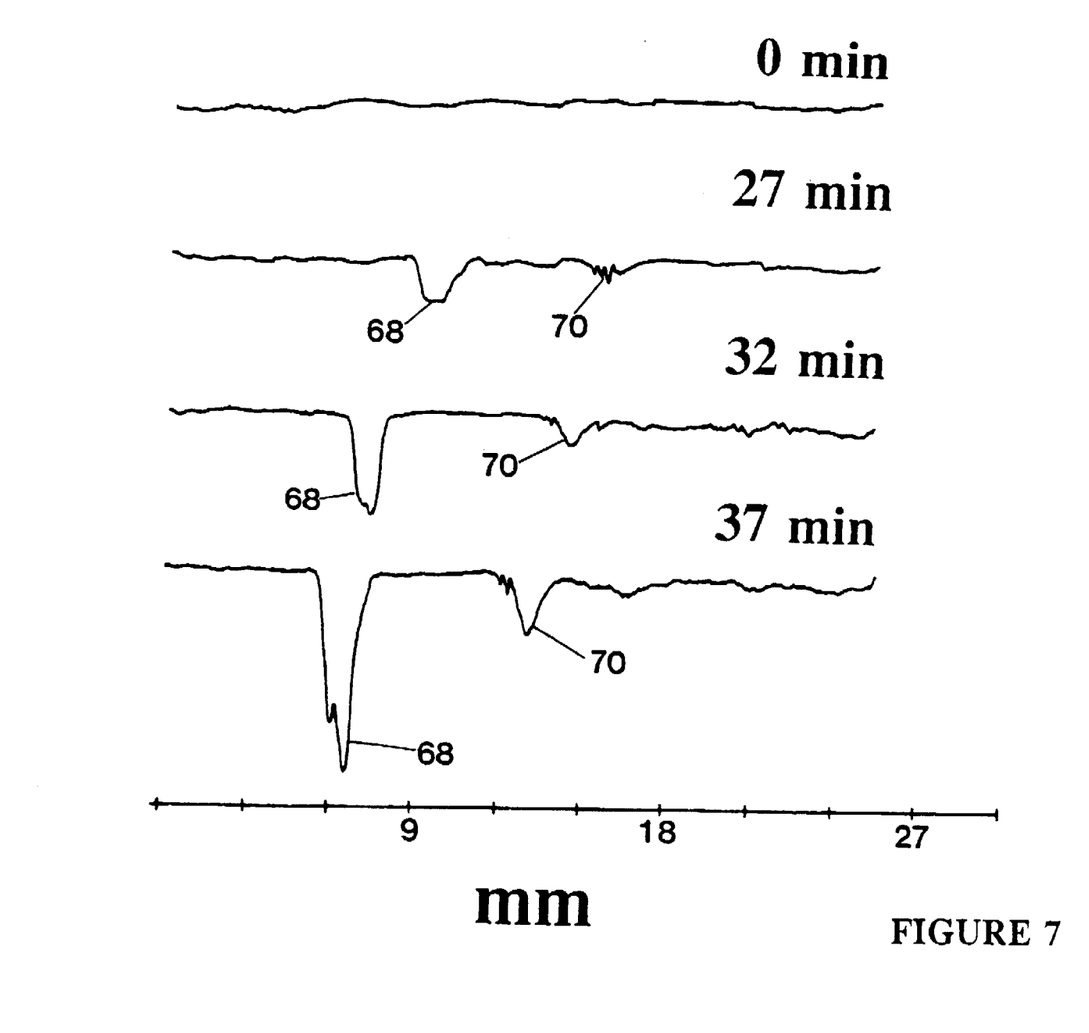
FIG. 7 shows the magnitude of successive absorption signals along the length of a capillary with a coated interior wall.

In FIG. 7, there is shown the magnitude of the absorption signal along the length of the capillary at 0 minutes, 27 minutes, 32 minutes and 37 minutes of isoelectric focusing. These results were obtained with an inside wall of the capillary coated with a non-cross-linked poly (acrylamide) to eliminate electroosmotic flow. In addition, agarose gel plugs were used at both ends of the capillary to reduce potential hydrodynamic flow. Initially, the cone-shaped capillary and two reservoirs (as shown in FIG. 1) were filled with a pH=7.3 TIRS buffer. Then, 1 kV of potential was supplied across the capillary for 10 minutes to achieve the uniform temperature and corresponding pH gradients. Then, a few drops of 0.1 mg/mL sample solution consisting of two forms of hemoglobin (methemoglobin, p1=7.20 and oxyhemoglobin p1=7.00) was introduced into the reservoir 4 at the wide end of the capillary containing the grounded electrode (cathode). Since the sample components have a slightly lower pI (by a fraction of a pH unit) compared to the chosen buffer pH, they are initially negatively charged and begin migrating through the capillary towards the positive electrode 10 until they reach their isoelectric point and the migration ceases. The analytes are trapped inside the capillary and, as expected, they form two narrow zones corresponding to methemoglobin 68 and oxyhemoglobin 70. It can be seen that the magnitude of the absorption signal progressively increases with time which confirms that the accumulation of analyte in the capillary occurs. In other words, the peaks increase in size with time. The width of the isoelectric focusing (IEF) bands can be estimated from the distance between the two forms of hemoglobin present in the sample (0.2 pH units) and corresponds to about 0.04 pH units. In FIG. 3, the estimated change in pH between the two ends of the cone-shaped capillary is about one pH unit. This corresponds to a temperature difference of about 40° C. between the two ends. To widen the pH range, buffers which have a larger temperature co-efficient of pH can be used. Also, the temperature differential can be increased by narrowing the smaller end of the capillary or by increasing the electrophoretic current by increasing the electrical potential. This approach might require cooling down the buffer reservoirs to prevent denaturing of proteins at high temperatures generated inside the capillary. Steady state temperature conditions were not reached in FIG. 3 even after 30 minutes since the bands were still changing position along the capillary between 32 minutes and 37 minutes. However, the drift that occurred between 32 minutes and 37 minutes was smaller than the drift that occurred between 27 minutes and 32 minutes and therefore the system was very close to reaching steady state temperature conditions.

Figure 8:
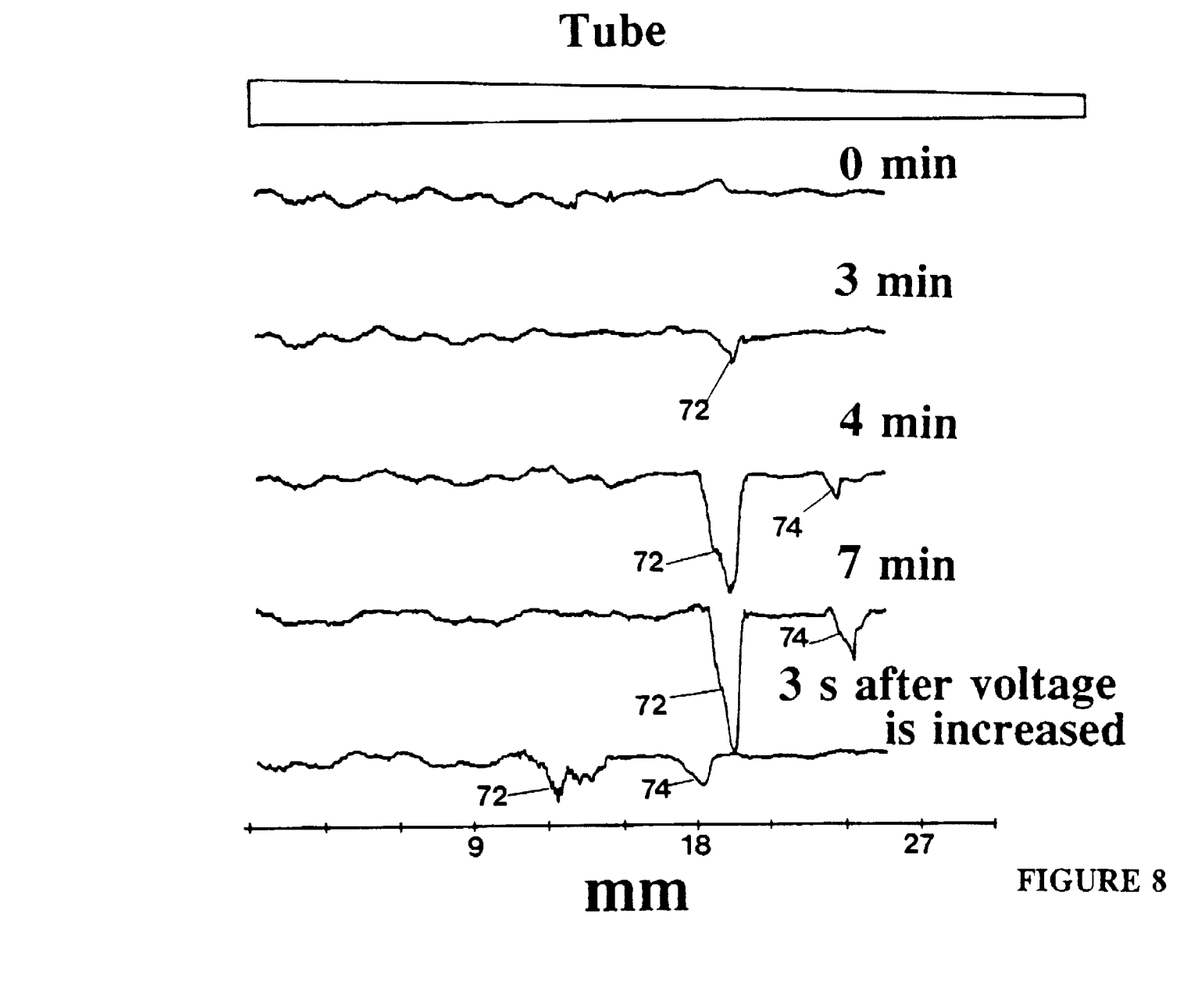
FIG. 8 shows the magnitude of successive absorption signals along the length of a capillary with an uncoated interior wall.

In FIG. 8, the magnitude of the absorption signal across the length of the capillary in successive times is shown. The cone-shaped capillary used to produce the results of FIG. 8 had an uncoated interior wall. The concentration of analyte in the buffer was about ten times higher than the concentration that produced the results for FIG. 7. The sample therefore accumulated much faster in the system of FIG. 8 than it did for the system in FIG. 7. The bands of analyte in FIG. 8 are not located in the appropriate isoelectric point, but rather at a somewhat higher pH at which electrophoretic velocity of the proteins are equal to the flow generated by electroosmosis. The electrolyte flow in the capillary cools the system and results in the pH values being shifted towards the narrow end of the capillary. The presence of the flow also produces more rapid thermal equilibration as indicated by the very stable analyte band position in the capillary. For example, it can be seen that a peak 72 lies at approximately the 19.5 mm location along the capillary after 3 minutes, after 4 minutes and after 7 minutes. The resolution in FIG. 8 decreased about 50% compared to the resolution in FIG. 7 and is most likely caused by the flow in the system.

The lowermost results in FIG. 8 were obtained after the separation voltage was increased from approximately 1 kV to approximately 1.5 kV. Analyte bands 72, 74 move towards the wider end of the capillary since the amount of heat generated in the capillary is increased and the pH values shift towards the cooler end. The intensity of the band is decreased because of the increase in the band's width and increase of the capillary diameter at the new position.

From FIG. 7, it can be seen that the isoelectric focusing technique of the present invention can be used not only for analytical and preparative separations but also for preconcentration and purification of biological samples prior to analysis. From FIG. 8, it can be seen that the isoelectric focusing system can be used for trapping and concentrating target ampholytes (for example, proteins, peptides, amino acids or any other substances having an isoelectric point) in the capillary followed by mobilization of analytes towards the detection or collection point by increasing the electrical potential.

EXAMPLE #1

Cone-shaped capillaries of 4 cm in length were used as the separation concentration channel and were drawn from 5 mm inside diameter glass tubes. The i. d. of one end of the capillary was 0.2 mm and another end was 1 mm. The capillary was mounted on a cartridge and its two ends were connected to buffer reservoirs as shown in FIG. 1. In some experiments, the inner wall of the capillary was coated with non-cross-linked poly (acrylamide) to eliminate electroosmosis by the reported way. Cross-linked poly (acrylamide) could also be used. The separation was driven by a high-voltage DC power supply (Spellman, Plainview, N.Y.), and the separation voltage was about 1 kV. The anode was inserted into the buffer reservoir at the narrower end of the capillary, and the another end of the capillary was connected to ground.

The protein sample used in the experiment was human hemoglobin (Sigma, St. Louis, Mo.) which contained two major isoforms; methemoglobin (75%) and oxyhemoglobin (25%). All chemicals were reagent grade, and solutions were prepared using deionized water. The buffer as 0.05 M TRIS buffer at pH 7.3. This buffer has a large temperature co-efficient of pH (dpH/dT is $-0.028K-1$ at $250°$ C.) (10). Protein solutions were prepared in the TRIS buffer. The solutions were filtered using 0.2-µm pore size cellulose acetate filters (Sartorius, Gottingen, Germany).

A UV-vis absorption imaging detector was employed for the monitoring of the protein zones focused inside the capillary. As shown in FIG. 2, the light source of the detector was a halogen lamp. The sensor was a 1024 pixel CCD (Type S3903-1024Q, Hammamatsu, Hammamatsu City, Japan). A bandpass coloured filter (400 nm–600 nm) was used to cut near IR and ultraviolet radiations of the lamp. The light beam was first collimated as shown in FIG. 2, and then focused into the capillary by three cylindrical lenses. The image of the capillary was projected into the CCD sensor as shown in FIG. 2.

Two sample introduction methods were used in the experiment. In the first method, the coated capillary was filled with the buffer, and plugs of 1% agarose gel (prepared in the buffer) were placed in both reservoirs to avoid hydrodynamic flow in the system, and then the voltage was applied. After 10 minutes, a few drops of 0.1 mg/mL sample solution was added to the top of the reservoir at the cathodic end of the capillary. In the second method, the reservoirs and the uncoated capillary were filled with the protein solution and the voltage was applied. In all experiments, the current passing through the capillary was kept at about 0.8 mA by adjusting the applied voltage to about 1 kV. All experiments were done in triplicate to ensure reproducibility.

In using the isoelectric focusing system of the present invention, the reservoir 6 at the narrow end of the capillary (anodic end) can be kept at a predetermined temperature to produce a low enough pH of the buffer to positively charge target proteins present in the reservoir (i.e. the sample that was added to the anodic reservoir). These proteins will then migrate through the capillary toward the cathode and will be trapped in the capillary at their isoelectric points or will be collected at the reservoir 4 connected to the wide end of the capillary. The system can be used to purify the biological material by fractionating it with respect to the isoelectric point. The cathodic end reservoir 4 will contain proteins which have a lower pI than the buffer in the reservoir 4 which is kept at room temperature. The anodic reservoir will contain proteins at a pI that is higher than the pH of the buffer in that reservoir while the capillary will contain proteins which have intermediate pI. The anodic reservoir 6 will be heated up in the process and that will speed up the concentration and focusing process when the sample is introduced to both the cathodic and anodic reservoirs.

Numerous variations, within the scope of the attached claims, will be readily apparent to those skilled in the art.

What I claim as my invention is:

1. A device used for isoelectric focusing of ampholytes contained in a buffer, said device comprising an elongated separation vessel with two ends, said vessel containing said buffer, said vessel having an elongated tapered portion so that a temperature gradient is created within contents of the vessel using a power source that generates a constant current, said power source having one terminal connected at one end of said vessel and another terminal connected at another end of said vessel, said power source connected to provide means with said tapered portion to create a temperature gradient longitudinally along said buffer in said vessel between said ends and to simultaneously focus said ampholytes with a detection system to monitor progress of said focusing.

2. A device as claimed in claim 1 wherein the seperation vessel has side walls that extend between the two ends, said walls smoothly tapering substantially from one end to the other to form the tapered portion.

3. A device as claimed in claim 2 wherein the walls have a linear taper.

4. A device as claimed in any one of claims 1 or 2 wherein the separation vessel is a tapered capillary.

5. A device as claimed in claim 1 wherein the separation vessel is a cone-shaped capillary.

6. A device as claimed in claim 5 wherein the power source is a DC power source, a positive electrode from said power source being connected into the buffer at a narrow end of said capillary and a negative electrode from said DC source being connected into the buffer at a wide end of said capillary.

7. A device as claimed in claim 6 wherein there is a reservoir at each end of the capillary, the reservoir containing said buffer and the electrodes being connected into said reservoir.

8. A device as claimed in claim 1 wherein the separation vessel contains an elongated channel of constant inside dimensions and has a conductive surface on an outside wall thereof, the conductive surface varying in thickness between said ends to form the tapered portion, a positive electrode being connected to said outside wall at a narrow end and a negative electrode being connected to said wall at a wide end.

9. A device as claimed in claim 8 wherein the power source is a DC power source and the narrow end has a higher temperature than the wide end.

10. A device as claimed in claim 8 wherein the conductive surface completely surrounds the outside wall of the elongated channel.

11. A device as claimed in any one of claims 1, 5 or 8 wherein the detection system is an absorption imaging detection system that continuously monitors the progress of said focusing and the separation vessel is transparent.

12. A device as claimed in any one of claims 1, 5 or 8 wherein an inner wall of the vessel is coated with a substance to eliminate electroosmotic flow.

13. A device as claimed in claim 10 wherein the device is used to focus proteins and the inner wall is coated with poly(acrylamide).

14. A device as claimed in any one of claims 1, 5 or 8 wherein the vessel has an inlet and an outlet located so that buffer can flow continuously through said vessel in a direction normal to a longitudinal axis of said vessel, with collection devices located at said outlet to collect a focused part of the buffer.

15. A device as claimed in claim 1 wherein the vessel has two side walls that converge with one another so that the vessel has a V-shaped cross-section, with an inlet and outlet located so that buffer can flow into and out of said vessel continuously in a direction normal to said cross-section.

16. A device as claimed in claim 15 wherein there is at least one collector at the outlet to collect part of the buffer that has been focused.

17. A method of isoelectric focusing of ampholytes contained in a buffer using an elongated separation vessel with two ends, said vessel having an elongated tapered portion so that a temperature gradient is created longitudinally within contents of the vessel using a constant current from a power source, a power source and an imaging detection system arranged to monitor progress of said focusing, said method comprising the steps of filling the vessel with a buffer containing ampholytes, connecting the power source to create a temperature gradient longitudinally along said buffer in said vessel and to focus said ampholytes, activating said power source and monitoring the progress of said focusing using said detection system.

18. A method of isoelectric focusing of ampholytes contained in a buffer using an elongated separation vessel with two ends, said vessel having physical characteristics such that a temperature gradient is created longitudinally within contents of the vessel using a constant current from a power source, a power source and an imaging detection system arranged to monitor progress of said focusing, said method comprising the steps of filling the vessel with a buffer containing ampholytes, said vessel not containing any carrier ampholytes, connecting the power source to create a temperature gradient longitudinally along said buffer in said vessel, and monitoring the progress of said focusing using said detection system.

19. A method as claimed in claim 18 including the steps of connecting the power source to create a temperature gradient longitudinally along said buffer in said vessel and to focus said ampholytes, and activating said power source.

20. A method as claimed in any one of claims 17, 18 or 19 including the step of choosing a power source so that a voltage across the vessel is substantially 1 kV.

21. A method as claimed in any one of claims 17, 18 or 19, including the step of choosing the power source so that a voltage across the vessel ranges from 100 volts per cm of length to 1 kV per cm of length.

22. A method of fractionating ampholytic components of biological material contained in a buffer using an elongated separation vessel with two ends, said vessel having physical characteristics such that a temperature gradient is created longitudinally within contents of the vessel using a constant current generated by a power source having one terminal connected at one end of said vessel and the other terminal connected at the other end, there being a reservoir for the terminals at each end of the vessel, one of the reservoirs being a cathodic reservoir and the other reservoir being an anodic reservoir, there being several separate anodic reservoirs, the method comprising the steps of activating the current until all components of the buffer having a pI, which is low enough, pass through the vessel into a first anodic reservoir, replacing the first anodic reservoir with a second anodic reservoir and activating the system with a slightly lower current than that which was used with the first reservoir, thereby causing part of the ampholytes located by focusing at one end of the vessel and having a low enough pI to be charged negatively and to migrate into the second anodic container, replacing the second anodic container with a third anodic container and repeating the process with an even lower current to cause another part of the ampholytes located by focusing at one end of the vessel with a low enough pI to migrate into the third anodic container, continuing to repeat the process with successive anodic containers and successive reductions in current until sufficient fractions of ampholytic components are obtained.

23. A method as claimed in claim 22 wherein the vessel is a cone-shaped capillary having a tip at one end and the tip of the capillary is dipped into successive anodic containers.

24. A method as claimed in any one of claims 19 or 20 wherein the vessel has an elongated tapered portion that constitutes the physical characteristics.

25. A method as claimed in any one of claims 19 or 20 wherein the vessel has an elongated tapered portion that extends substantially from one end to the other to constitute said physical characteristics.

26. A method as claimed in any one of claims 19 or 20 wherein the vessel is a tapered capillary.

27. A method as claimed in any one of claims 19 or 20 wherein the vessel is a cone-shaped capillary.

28. A device as claimed in any one of claims 1, 2 or 3 wherein the vessel has an inlet at one end and an outlet at another end so that said buffer can flow through said vessel parallel to longitudinal axis of said vessel.

* * * * *